United States Patent [19]
Purchio et al.

[11] Patent Number: 5,599,788
[45] Date of Patent: Feb. 4, 1997

[54] METHOD FOR ACCELERATING SKIN WOUND HEALING WITH H3 PROTEIN

[75] Inventors: Anthony F. Purchio, Cardiff; Richard LeBaron, Temecula, both of Calif.

[73] Assignee: Advanced Tissue Sciences, La Jolla, Calif.

[21] Appl. No.: 268,797

[22] Filed: Jul. 1, 1994

[51] Int. Cl.$^6$ ............................... A61K 9/10; C07K 17/08
[52] U.S. Cl. ............................... 514/2; 514/12; 514/885; 514/886; 514/887; 514/944; 514/945; 514/946; 514/947; 424/409; 424/278.1
[58] Field of Search .................. 424/85.1, 278.1, 424/413, 443–447; 514/2, 8, 12, 885–887, 944–947, 969; 530/399

[56] References Cited

U.S. PATENT DOCUMENTS

| | | | |
|---|---|---|---|
| 4,721,096 | 1/1988 | Naughton et al. | 435/240 |
| 4,963,489 | 10/1990 | Naughton et al. | 435/240.1 |
| 5,444,164 | 8/1995 | Purchio et al. | 536/23.5 |

FOREIGN PATENT DOCUMENTS 9214480  9/1992  WIPO.

OTHER PUBLICATIONS

Mustoe et al. (1987) Science vol. 237 pp. 1333–1335.
Jones et al. (1991) J. of Surgical Res. vol. 51 pp. 344–352.
Le Baron et al. (1995) J. Invest. Dermatol. vol. 104, pp. 844–849.
Agrez, M. et al. (1991) Arg–Gly–Asp–containing peptides expose novel collagen receptors on fibroblasts: implications for wound healing. Cell Regulation 2:1035–1044.
Barnard, J. et al. (1990) The cell biology of transforming growth factor β. Biochimica et Biophysica Acta 1032:79–87.
Bebbington, C. R. et al. (1992) High–level expression of a recombinant antibody from myeloma cells using a glutamine synthetase gene as an amplifiable selectable marker. Biotechnology 10:169–175.
Cate, R. L. et al. (1986) Isolation of the bovine and human genes for Müllerian inhibiting substance and expression of the human gene in animal cells. Cell 45:685–698.
Cockett, M. I. et al. (1990) High level expression of tissue inhibitor of metalloproteinases in chinese hamster ovary cells using glutamine synthitase gne amplification. Biotechnology 8:662–667.
Dustin, M. et al. (1989) T–cell receptor cross–linking transiently stimulates adhesiveness through LFA–1. Nature 341:619–624.
Gentry, L. et al. (1988) Molecular events in the processing of recombinant type 1 pre–pro–transfering growth factor beta to the mature polypeptide. Molecular and Cellular Biology 8(10):4162–4168.
Goey, H. et al. (1989) Inhibition of early murine hemopoietic progenitor cell proliferation after in vivo locoregional administration of transforming growth factor–β1[1]. The Journal of Immunology 143(3):877–880.
Graf, J. et al. (1987) Identification of an amino acid sequence in laminin mediating cell attachment chemotaxis, and receptor binding. Cell 48:989–996.

Hemler, Martin E. (1990) VLA proteins in the integrin family: structures, functions, and their role on leukocytes[1]. Annu. Rev. Immunol. 8:365–400.
Hynes, Richard O. (1992) Integrins: versatility, modulation, and signaling in cell adhesion. Cell. 69:11–25.
Ignotz, R. et al. (1986) Transforming growth factor–β stimulates the expression of fibronectin and collagen and their incorporation into the extracellular matrix*. The Journal of Biological Chemistry 261(9):4337–4345.
Landegren, Ulf (1984) Measurement of cell numbers by means of the endogenous enzyme hexosaminidase. Applications to detection of lymphokines and cell surface antigens. Journal of Immunological Methods 67:379–388.
Mason, A. et al. (1985) Complementary DNA sequences of ovarian follicular fluid inhibin show precursor structure and homology with transforming growth factor–β. Nature 318:659–663.
Matsudaira, Paul (1987) Sequence from picomole quantities of proteins electroblotted onto polyvinylidene difluoride membranes*. The Journal of Biological Chemistry 262(21):10035–10038.
Mustoe, T. et al. (1987) Accelerated healing of incisional wounds in rats induced by transforming growth factor–β. Science 237:1333–1335.
Noda, M. et al. (1989) In vivo stimulation of bone formation by transforming growth factor–β. Endocrinology 124(6):2991–2994.
Pietenpol, J. et al. (1990) Transforming growth factor β1 suppression of c–myc gene transcription: role in inhibition of keratinocyte proliferation. Proc. Natl. Acad. Sci. 87:3758–3762.
Quaglino Jr., D. et al. (1991) Transforming growth factor–beta stimulates wound healing and modulates extracellular matrix gene expression in pig skin: incisional wound model. J. Invest. Dermatol. 97:34–42.
Ruoslahti, Erkki (1991) Integrins. J. Clin. Invest. 87:1–5.
Skonier, J. et al. (1992) cDNA cloning and sequence analysis of βig–h3, a novel gene induced in a human adenocarcinoma cell line after treatment with transforming growth factor–β. DNA and Cell Biology 11(7):511–522.
Warren, W. et al. (1992) Tissue repair by thrombin–derived peptides in the rat. Peptide Research 5(6):331–335.
Chen, T., et al. (1992) Human recombinant transforming growth factor–β1 modulation of biochemical and cellular events in healing of ulcer wounds. The Journal of Investigative Dermatology 98:428–435.
Zioncheck, T., et al. (1994) Pharmacokinetics and tissue distribution of recombinant human transforming growth factor beta$_1$ after topical and intravenous administration in male rats. Pharmaceutical Research 11(2):213–220.

*Primary Examiner*—John Ulm
*Assistant Examiner*—Prema Mertz
*Attorney, Agent, or Firm*—Knobbe, Martens, Olson & Bear

[57] ABSTRACT

A method of producing recombinant transforming growth factor β-induced H3 protein and the use of this protein to accelerate wound healing. H3 promoted adhesion of human dermal fibroblasts to tissue culture plastic. The protein is applied directly to a wound or is used to promote adhesion and spreading of dermal fibroblasts to a solid support such as a nylon mesh which is then applied to the wound. In addition, CHO cells expressing H3 inhibited tumor cell growth.

8 Claims, 4 Drawing Sheets

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 2049 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:1:

```
ATGGCGCTCT    TCGTGCGGCT    GCTGGCTCTC    GCCCTGGCTC    TGGCCCTGGG    CCCCGCCGCG    60

ACCCTGGCGG    GTCCGCCAA     GTCGCCCTAC    CAGCTGGTGC    TGCAGCACAG    CAGGCTCCGG    120

GGCCGCCAGC    ACGGCCCCAA    CGTGTGTGCT    GTGCAGAAGG    TTATTGGCAC    TAATAGGAAG    180

TACTTCACCA    ACTGCAAGCA    GTGGTACCAA    AGGAAAATCT    GTGGCAAATC    AACAGTCATC    240

AGCTACGAGT    GCTGTCCTGG    ATATGAAAAG    GTCCCTGGGG    AGAAGGGCTG    TCCAGCAGCC    300

CTACCACTCT    CAAACCTTTA    CGAGACCCTG    GGAGTCGTTG    GATCCACCAC    CACTCAGCTG    360

TACACGGACC    GCACGGAGAA    GCTGAGGCCT    GAGATGGAGG    GGCCCGGCAG    CTTCACCATC    420

TTCGCCCCTA    GCAACGAGGC    CTGGGCCTCC    TTGCCAGCTG    AAGTGCTGGA    CTCCCTGGTC    480
```

```
AGCAATGTCA ACATTGAGCT GCTCAATGCC CTCGCGTACC ATATGGTGGG CAGGCGAGTC      540
CTGACTGATG AGCTGAAACA CGGCATGACC CTCACCTCTA TGTACCAGAA TTCCAACATC      600
CAGATCCACC ACTATCCTAA TGGGATTGTA ACTGTGAACT GTGCCCGGCT CCTGAAAGCC      660
GACCACCATG CAACCAACGG GGTGGTGCAC CTCATCGATA AGGTCATCTC CACCATCACC      720
AACAACATCC AGCAGATCAT TGAGATCGAG GACACCTTTG AGACCCTTCG GGCTGCTGTG      780
GCTGCATCAG GGCTCAACAC GATGCTTGAA GGTAACGGCC AGTACACGCT TTTGGCCCCG      840
ACCAATGAGG CCTTCGAGAA GATCCCTAGT GAGACTTTGA ACCGTATCCT GGGCGACCCA      900
GAAGCCCTGA GAGACCTGCT GAACAACCAC ATCTTGAAGT CAGCTATGTG TGCTGAAGCC      960
ATCGTTGCGG GGCTGTCTGT AGAGACCCTG GAGGGCACGA CACTGGAGGT GGGCTGCAGC     1020
GGGGACATGC TCACTATCAA CGGGAAGGCG ATCATCTCCA ATAAAGACAT CCTAGCCACC     1080
AACGGGGTGA TCCACTACAT TGATGAGCTA CTCATCCCAG ACTCAGCCAA GACACTATTT     1140
GAATTGGCTG CAGAGTCTGA TGTGTCCACA GCCATTGACC TTTTCAGACA AGCCGGCCTC     1200
GGCAATCATC TCTCTGGAAG TGAGCGGTTG ACCCTCCTGG CTCCCCTGAA TTCTGTATTC     1260
AAAGATGGAA CCCCTCCAAT TGATGCCCAT ACAAGGAATT TGCTTCGGAA CCACATAATT     1320
AAAGACCAGC TGGCCTCTAA GTATCTGTAC CATGGACAGA CCCTGGAAAC TCTGGGCGGC     1380
AAAAAACTGA GAGTTTTGT TTATCGTAAT AGCCTCTGCA TTGAGAACAG CTGCATCGCG     1440
GCCCACGACA AGAGGGGGAG GTACGGGACC CTGTTCACGA TGGACCGGGT GCTGACCCCC     1500
CCAATGGGGA CTGTCATGGA TGTCCTGAAG GGAGACAATC GCTTAGCAT GCTGGTAGCT     1560
GCCATCCAGT CTGCAGGACT GACGGAGACC CTCAACCGGG AAGGAGTCTA CACAGTCTTT     1620
GCTCCCACAA ATGAAGCCTT GCGAGCCCTG CCACCAAGAG AACGGAGCAG ACTCTTGGGA     1680
GATGCCAAGG AACTTGCCAA CATCCTGAAA TACCACATTG GTGATGAAAT CCTGGTTAGC     1740
GGAGGCATCG GGCCCTGGT GCGGCTAAAG TCTCTCCAAG GTGACAAGCT GGAAGTCAGC     1800
TTGAAAAACA ATGTGGTGAG TGTCAACAAG GAGCCTGTTG CCGAGCCTGA CATCATGGCC     1860
ACAAATGGCG TGGTCCATGT CATCACCAAT GTTCTGCAGC CTCCAGCCAA CAGACCTCAG     1920
GAAAGAGGGG ATGAACTTGC AGACTCTGCG CTTGAGATCT TCAAACAAGC ATCAGCGTTT     1980
TCCAGGGCTT CCCAGAGGTC TGTGCGACTA GCCCCTGTCT ATCAAAAGTT ATTAGAGAGG     2040
ATGAAGCAT                                                             2049
```

METHOD FOR ACCELERATING SKIN WOUND HEALING WITH H3 PROTEIN

FIELD OF THE INVENTION

The present invention relates to cellular proteins which regulate cell adhesion. In particular, the invention relates to a cellular protein induced by Transforming Growth Factor-$\beta_1$ (TGF-$\beta_1$) which promotes the adhesion of human dermal fibroblasts and inhibits the adhesion of a number of transformed human cell lines including lung fibroblasts and HeLa cells. The invention also relates to the production of recombinant H3 in Chinese hamster ovary cells and the inhibition of tumor growth in mice injected with these cells.

BACKGROUND OF THE INVENTION

Cell adhesion is involved in a number of critical cellular processes including anchorage to the extracellular matrix and to other cells, growth, differentiation and migration. Cell adhesion is mediated by dimeric transmembrane receptor proteins called integrins (Ruoslahti, (1991) *J. Clin. Invest.*, 87:1–5; Hynes, (1992) *Cell*, 69:11–25). Integrins promote cell adhesion to the extracellular matrix, a filamentous network of proteins secreted by cells, by binding to target sequences present in these proteins. The major target sequence recognized by integrins is an arginine-glycine-aspartate (RGD) motif present in numerous substrate proteins including fibronectin, vitronectin and laminin (Hemler, (1990) *Annu. Rev. Immunol.*, 8:365–400). First identified in fibronectin, RGD has since been shown to be the cellular recognition sequence in many matrix proteins. Other sequence motifs have also been found to promote cell adhesion, including KQAGD found in fibrinogen and PDSGR found in laminin.

TGF-$\beta$ encompasses a family of dimeric proteins including TGF-$\beta$1, TGF-$\beta$2, TGF-$\beta$3, TGF-$\beta$4, and TGF-$\beta$5 which regulate the growth and differentiation of many cell types (Barnard et al., (1990) *Biochim. Biophys. Acta.*, 1032:79–87). Other members of this family include the more distantly related Mullerian inhibitory substance (Cate et al., (1986) Cell, 45:685–698) and the inhibins (Mason et al., (1985) *Nature*, 318:659–663). TGF exhibits a diverse range of biological effects, stimulating the growth of some cell types (Noda et al., (1989) *Endocrinology*, 124:2991–2995) and inhibiting the growth of other cell types (Goey et al., (1989) *J. Immunol.*, 143:877–880; Pietenpol et al., (1990) *Proc. Natl. Acad. Sci. USA*, 87:3758–3762). In regard to cell adhesion, TGF-$\beta$ increases the expression of collagen and fibronectin (Ignotz et al., (1986) *J. Biol. Chem.*, 261:4337–4345) and accelerates the healing of incisional wounds (Mustoe et al., (1987) *Science*, 237:1333–1335).

Skonier et al. (*DNA Cell Biol.*, 11:511–522, 1992) cloned and sequenced a TGF-$\beta$1-induced gene isolated from a human lung adenocarcinoma cell line by constructing cDNA libraries from both TGF-$\beta$1-stimulated and unstimulated cells and screening the libraries by subtractive hybridization. This gene encoded a 683 amino acid protein called $\beta$IG-H3 (H3) which contained a carboxy-terminal RGD sequence. The protein also contained four internal repeats with limited homology to Drosophila fasciclin I, an extrinsic membrane protein thought to be involved in growth cone guidance, and a PDSAK sequence similar to the PDSGR active binding domain of laminin. The presence of these sequence motifs indicated that H3 could be involved in cell adhesion.

Numerous attempts have been made at increasing fibroblast adhesion to substrates. The main approach has involved the use of RGD-containing peptides (Quaglino, Jr., et al., (1991) *J. Invest. Dermatol.*, 97:34–42; *Peptide Res.*, 5:331–335; Agrez et al., (1991) *Cell Regul.*, 2:1035–1044), although this method has had limited success. U.S. Pat. No. 4,963,489 to Naughton et al., the contents of which are hereby incorporated by reference, discloses a three-dimensional matrix and its use as a framework for a multi-layer cell culture system for the production of a number of cells and/or tissues by culturing desired cell types on a stromal cell layer.

There are currently no simple, effective methods for stimulating cell spreading and adhesion at wound sites to promote rapid wound healing. Thus, there is a need for substances able to promote attachment and spreading of cells, particularly fibroblasts, to facilitate this important process. Such a substance and its use in wound healing and tissue engineering applications are described herein.

SUMMARY OF THE INVENTION

One embodiment of the present invention is a method for enhancing the attachment of cells to a solid support by coating the support with an effective cell attachment-enhancing amount of H3 protein prior to contacting the support with the cells. Preferably, the cells are mammalian; most preferably, the cells are human. Further, the cells may be either fibroblasts, epithelial cells or keratinocytes. Advantageously, the H3 is recombinant or derived from human fibroblasts. According to another aspect of this preferred embodiment, the solid support is a three dimensional scaffold which may be in the form of a sheet or mesh. Suitable materials for the solid support include polytetrafluoroethylene, polystyrene, polypropylene, polyacrylates, polyvinyl compounds, polycarbonate, nitrocellulose, cellulose, polyglycolic acid, catgut sutures and gelatin.

The invention also provides an article of manufacture comprising a solid support coated with H3. Preferably, the solid support is a three-dimensional scaffold which may be either a sheet or mesh. Suitable materials for the solid support include polytetrafluoroethylene, polystyrene, polypropylene, polyacrylates, polyvinyl compounds, polycarbonate, nitrocellulose, cellulose, polyglycolic acid catgut sutures and gelatin. Advantageously, the H3 is either recombinant or derived from human fibroblasts.

Another embodiment of the invention is a method for inhibiting tumor growth comprising contacting the tumor with a DNA construct operably encoding H3. This method may further comprise radiation and chemotherapy treatment.

The invention further provides a method for accelerating wound healing by contacting the wound with an effective healing-promoting amount of H3. Preferably, the H3 is contained in a topical pharmaceutical formulation consisting of an aqueous solution, gel, cream, paste, lotion, spray, suspension, dispersion, salve or ointment. In accordance with another aspect of this embodiment, the H3 is either recombinant or derived from human fibroblasts. Preferably, the wound is either a skin ulcer, burn, laceration or surgical incision.

Still another embodiment of the invention is a shaped article comprising a solid support, H3 protein coated onto the support and cells adhering to the H3-coated solid support. Preferably, the solid support is a three dimensional scaffold which may be either a sheet or mesh. Preferably, the sheet is made of either polytetrafluoroethylene, polystyrene, polypropylene, polyacrylates, polyvinyl compounds, polycarbonate, nitrocellulose, cellulose, polyglycolic acid, catgut sutures or gelatin. According to another aspect of this embodiment, the cells are fibroblasts, epithelial cells or keratinocytes.

The invention also provides a method for accelerating wound healing comprising applying the solid support mentioned hereinabove to the wound.

According to another aspect of the invention, there is provided a pharmaceutical composition comprising H3 in a pharmaceutically acceptable carrier. Preferably, the carrier is either an aqueous solution, gel, cream, paste, lotion, spray, suspension, salve or ointment.

Yet another embodiment of the invention is a method for accelerating wound healing comprising contacting the wound at least daily with between about 10 μg and about 10 mg H3.

Further, the invention provides a method for accelerating wound healing comprising contacting the wound with a shaped article, the shaped article comprising a solid support coated with between about 0.1 μg/mm² and about 10 μg/mm² H3 protein and fibroblasts adhering to the H3 protein.

According to another aspect of the invention, there is provided a method of producing recombinant H3 protein comprising the following steps:

inserting the DNA sequence encoding H3 into an expression vector containing a selectable marker, the H3 DNA sequence in operable juxtaposition to a heterologous promoter;

transfecting chinese hamster ovary cells with the expression vector;

culturing the cells in a selection medium;

selecting and expanding positive clones; and purifying the H3 protein.

Preferably, the promoter is the cytomegalovirus promoter and the expression vector is pEE-14.

DETAILED DESCRIPTION OF THE INVENTION

Figure 1:
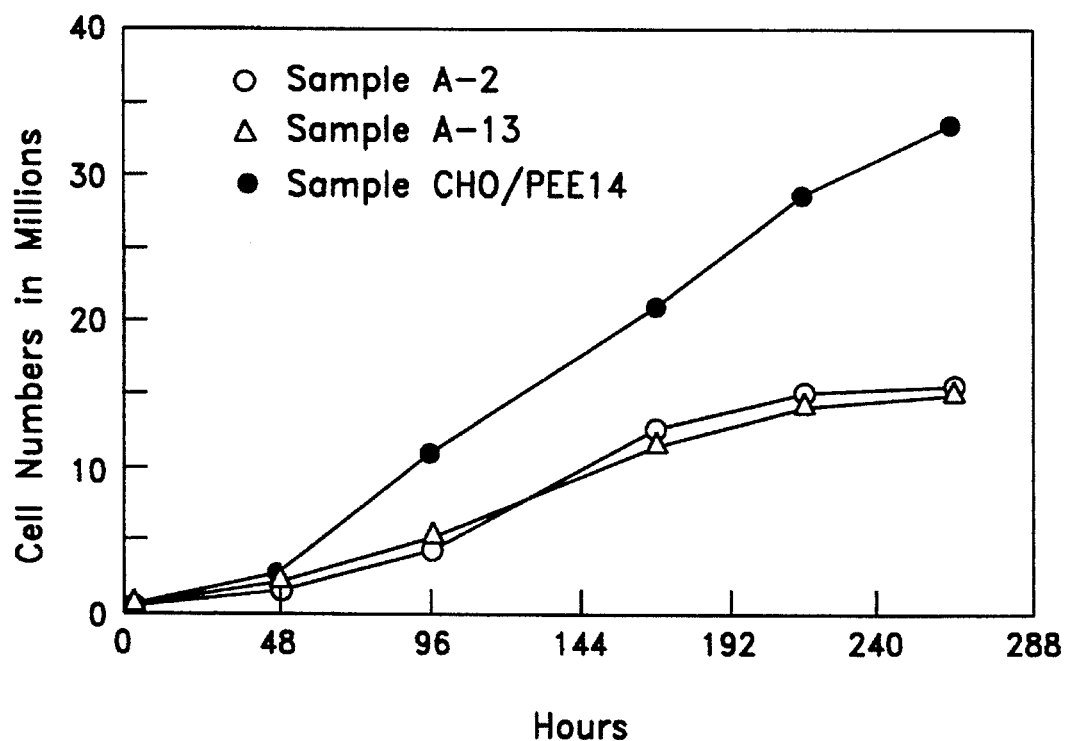
FIG. 1 shows the H3-mediated inhibition of A549 cell adhesion. Tissue culture wells were coated with either varying amounts of purified recombinant H3 protein or control pEE-14 media and 5×10⁵ A549 cells were incubated in the wells for two hours at 37° C. Wells were washed with PBS and the remaining attached cells were counted. The x-axis shows the amount of H3 used (μg) and the y-axis shows the number of attached A549 cells.

The present invention discloses the stimulatory and inhibitory action of the TGF-β1-induced H3 protein on cell adhesion. In addition, the production of recombinant H3 in CHO cells and the H3-mediated inhibition of tumor formation is also disclosed.

Recombinant H3 protein was produced in Chinese hamster ovary (CHO) cells by transfecting a DNA construct containing the cDNA encoding H3 operably linked to a cytomegalovirus (CMV) promoter. A number of promoters well known in the art are also contemplated including the Simian Virus 40 (SV40), Rous sarcoma virus (RSV), adenovirus and any other promoter capable of being operably linked to H3 such that production of recombinant protein occurs in transfected mammalian cells. The construct also preferably contains a eukaryotic selectable marker encoding drug resistance to allow identification of positive transfectants. Nonlimiting examples of such selectable markers include methionine sulfoxide (MSX), dihydrofolate reductase, hygromycin and neomycin. Transfection may be accomplished by a number of techniques well known in the art, including but not limited to calcium phosphate precipitation, lipofection, electroporation, and DEAE-dextran mediated delivery. The transfected cells are then cultured in a medium containing a toxic substance to allow selection of transfectants expressing the drug resistance gene. These positive clones are pooled and expanded using conventional tissue culture techniques.

Since the H3 protein is secreted, it accumulates in the conditioned medium of the H3 CHO transfectants. The protein may then be isolated by conventional protein purification techniques well known in the art. The preferred method of isolation involves ammonium sulfate precipitation and gel filtration column chromatography, although any other purification method including, but not limited to, affinity chromatography, ion exchange chromatography, adsorption chromatography and high performance liquid chromatography is also contemplated.

H3 protein is also produced by human foreskin fibroblasts, both in their unstimulated and TGF β1-stimulated states; however, the level of H3 produced is increased in TGF β1-stimulated cells. The protein is secreted by the fibroblasts and accumulates in the culture medium.

Since the H3 protein both inhibited and promoted cell adhesion, it has applications in cancer therapy and wound healing. H3 inhibited the adhesion of the A549, HeLa and WI-38 transformed cell lines, indicating its utility as an inhibitor of cancer cell adhesion to both other cells and to the extracellular matrix. Importantly, CHO cells transfected with the H3 cDNA were severely compromised in their ability to form tumors in immunosuppressed mice compared to control cells transfected with the vector alone. Thus, H3 will have utility in gene therapy. Tumor cells transfected in vivo with a DNA construct encoding H3 operably linked to a heterologous promoter will be growth inhibited. Gene therapy using H3 may be combined with conventional chemotherapy and radiation treatment to increase the overall treatment efficacy. Methods of introduction of the DNA construct to tumor cells include direct injection and intravenous administration of an antibody-DNA conjugate in which the antibody has affinity for a tumor cell antigen and is internalized by the tumor cell.

H3 was also determined to specifically promote the adhesion of human dermal fibroblasts to tissue culture plates. Thus, H3 will have utility in promoting wound healing, a process in which increased fibroblast adhesion and spreading is desired. Such wounds include burns, skin ulcers, lacerations, surgical incisions and the like. The recombinant H3 protein may be directly applied to the wound in a sterile physiological solution such as saline in an effective fibroblast adhesion-accelerating amount. This is a simple method which does not require growing fibroblasts prior to application to the wound and obviates the need to obtain an individual's own cells for treatment.

Alternatively, the H3 may be incorporated into a pharmaceutical composition. Nonlimiting examples of particularly preferred compositions of H3 for topical administration include lotions, creams, gels, salves, sprays, dispersions, suspensions, pastes and ointments. The preparations may further advantageously include preservatives, antioxidants, antibacterials, antifungals, antiosmotic agents and similar materials in composition and quantity as is conventional. For assistance in formulating the compositions of the present invention, one may refer to Remington's Pharmaceutical Sciences, 15th Ed., Mack Publishing Co., Easton, Pa. (1975), the relevant disclosure of which is hereby incorporated by reference.

Although the amount applied and frequency of application will vary depending on the severity and size of the wound, contemplated amounts of H3 range from about 10 µg to about 10 mg per application. The composition may be applied daily, every other day or every several days.

In another embodiment, a shaped article such as a three dimensional scaffold, fabric, sheet, mesh or other appropriate article may be coated with H3. Although the amount of H3 used to coat the article will vary depending on the size and composition of the article, it is estimated that between about 0.1 µg and about 100 µg per mm$^2$ will be sufficient. The article may be coated by spraying with or immersion in a solution containing H3 in a concentration ranging from about 10 µg/ml to about 10 mg/ml. In a preferred embodiment, the concentration of H3 is between about 50 µg/ml and about 1 mg/ml. Other coating methods are also within the scope of the invention. The optimum coating amount of H3 for promoting cell attachment to a solid support may easily be determined by one of ordinary skill in the art.

The article may be constructed of a number of inert, biocompatible, nontoxic materials including nylon, polyester, polytetrafluoroethylene (PTFE), polystyrene, polypropylene, polyacrylates, polyvinyl compounds, polycarbonate, nitrocellulose, cellulose, polyglycolic acid (PGA), catgut sutures, gelatin, or any material to which H3 can be applied and to which fibroblasts will adhere. Any of these materials may be woven into a mesh to form a three-dimensional matrix. One suitable nylon mesh for use in the present invention is NITEX™, a nylon filtration mesh having an average pore size of 210 µm and an average nylon fiber diameter of 90 µm (Tetko, Inc., New York).

Cells are then cultured on the H3-coated article under standard growth conditions including nutrients, antibiotics and growth factors, resulting in a three dimensional array of cells. Although human cells are preferred, cells from other mammals including, but not limited to, monkeys, mice and rabbits are also contemplated. Other cell types suitable for application to the H3-coated article include keratinocytes, epithelial cells, epidermal cells and any desired cell type capable of adhering to the H3-coated article. One having ordinary skill in the art of cell biology could easily determine whether a given cell type was capable of binding to an H3-coated article.

Although cells may be obtained from a number of sources including fetal and adult tissues, they are preferably isolated from the same individual who is to later receive the transplanted/implanted cells and/or tissues grown according to the present invention so as to reduce the chance of immunological rejection. The resulting three dimensional array of cells is structurally analogous to in vivo tissue.

The three dimensional culture may be transplanted or implanted into a patient, seeding the damaged area and providing a nucleus for subsequent cell attachment, resulting in accelerated closure of the wounded area. This will promote healing by stimulating proliferation of cells in the surrounding tissue. Transplanted fibroblast cultures on wound sites will decrease the chances of bacterial infection by serving as a barrier, similar to normal skin. The three dimensional culture may be used as either a permanent treatment or may serve as a temporary barrier to infection and fluid loss until a skin graft can be performed. Where the three-dimensional culture is to be implanted in vivo, it may be preferable to use biodegradable matrices such as PGA, catgut suture material or gelatin, for example.

To obtain sufficient amounts of recombinant H3 protein for in vitro analysis, the cDNA was expressed in mammalian cells as described below.

EXAMPLE 1

Production of Recombinant H3

The glutamine synthetase expression system (Celltech, Berkshire, United Kingdom) was used to express H3 in recombinant chinese hamster ovary (CHO) cells (Cockett et al., (1990) *Biotechnology*, 8:662–667; Bebbington et al., (1992) *Biotechnology*, 10:169–175). The H3 coding region (Skonier et al., (1992) *DNA Cell Biol.*, 11:511–522; SEQ ID NO: 1) was cloned into the expression vector pEE-14 which contains a cytomegalovirus (CMV) promoter (Celltech) and transfected into CHO cells using calcium phosphate precipitation as instructed by the manufacturer. Transfectants were selected using 25 µM methionine sulfoxide (MSX) and individual clones were selected and expanded. Clones secreting H3 were identified by immunoblotting of conditioned serum-free medium with a polyclonal antibody to H3. Positive clones were designated CHO/H3cl.A13, CHO/H3cl.A19 and CHO/H3cl.A2g. Control CHO cells transfected with empty vector are designated as control CHO/pEE-14 cells.

When immunoblotting was performed after SDS-PAGE analysis under non-reducing conditions, CHO/H3cl.A13 cells secreted a protein migrating on SDS gels at about 68 kDa. This protein was not secreted in cells transformed with the vector alone. The protein was absent in control CHO cells. When immunoblotting was performed after SDS-PAGE under reducing conditions, three closely spaced bands were observed which were absent in control CHO cells. Since there are no predicted sites of N-linked glycosylation in the deduced βIG-H3 protein sequence (Skonier et al., 1992), and since neuraminidase treatment did not affect electrophoretic mobility, the observed heterogeneity may be due to carboxy-terminal processing, sulfation or methylation.

The secreted recombinant H3 protein was purified and sequenced as described below.

EXAMPLE 2

Purification of Recombinant H3

Serum-free conditioned medium from CHO/H3cl.A13 cells was precipitated with 50% ammonium sulfate at 4° C. for 20 hours and centrifuged for 30 minutes at 30,000×g.

The pellet was dissolved in phosphate buffered saline (PBS) and applied to a BioSil TSK-250 gel filtration column (BioRad, Richmond, Calif.) equilibrated with PBS. Fractions containing H3 were identified by immunoblotting, pooled, aliquoted and stored at −70° C.

Proteins were fractionated by SDS-PAGE and transferred to a ProBlott membrane (Applied Biosystems, Foster City, Calif.) using a mini-transblot electrophoretic transfer cell (BioRad) as previously described (Matsudaira, (1987) *J. Biol. Chem.*, 262:10035–10038). The membrane was stained with Coomassie Brilliant Blue, destained and the 68 kDa band was excised for amino-terminal sequence analysis.

Samples were sequenced in a pulsed-liquid phase protein sequencer (Applied Biosystems model 476A) equipped with a vertical cross-flow reaction cartridge. The phenylthiohydantoin (pth) amino acid derivatives were analyzed by reversed-phase high performance liquid chromatography (HPLC). Data reduction and quantitation were performed on a Macintosh IIsi computer (Apple Computers, Inc.) and model 610A chromatogram analysis software (Applied Biosystems).

Since the growth rate of the CHO/H3cl.A13 and CHO/H3cl.A2g clones was slower than that of the control cells (FIG. 1) and since the two clones reached an overall lower saturation density, the tumorigenicity of the cells was assessed as described below.

EXAMPLE 3

Reduced Tumorigenicity of CHO Cells Expressing H3

Three independently selected H3-expressing clones were injected ($3 \times 10^7$ cells per injection) subcutaneously into the backs of female athymic nude mice (Harlan Sprague Dawley, Indianapolis, Ind.) and tumors were evaluated at 4 weeks. As shown in Table 1, while the control cells readily formed tumors, CHO cells expressing H3 were significantly impaired in their ability to form tumors. The single tumor arising from the CHO/H3cl.A13 cells remained small (3×3 mm) over 10 weeks of observation, while the control cells typically produced a tumor measuring 15×20 mm by 4 weeks.

TABLE 1

| Clone | # tumors/# animals injected |
| --- | --- |
| Control CHO/pEE-14 | 8/10 |
| CHO/H3cl.A19 | 0/10 |
| Control CHO/pEE-14 | 8/10 |
| CHO/H3cl.A13 | 1/10 |
| Control CHO/pEE-14 | 7/10 |
| CHO/H3cl.A2g | 0/10 |

Since H3 is a secreted protein with four regions of internal homology to fasciclin I and contains an RGD motif common in proteins modulating cell attachment, an adhesion assay using various human cell lines was performed as described in the following example.

EXAMPLE 4

Inhibition of Cell Adhesion by H3

A549 human lung adenocarcinoma (American Type Culture Collection (ATCC), Rockville, Md., ATCC CCL 185), HeLa (ATCC CCL 2), WI-38 human lung fibroblasts (ATCC CCL 75) and CHO cells (ATCC CRL 9096) were grown in Dulbecco's Modified Eagle Medium (DMEM) containing 10% fetal calf serum (FCS).

Cell adhesion assays similar to those used to identify proteins and their active domains involved in cell attachment were carried out on H3 attached to Costar 6-well plates (Graf et al., (1987) *Cell*, 48:989–996; Dustin et al., (1989) *Nature*, 341:619–624). Individual wells of a 24-well tissue culture dish were incubated for 2 hours at 22° C. with 7.5 μg purified recombinant H3, BSA or serum-free medium from control CHO/pEE-14 cells purified in a similar fashion to H3. A549 cells ($2 \times 10^5$ cells/well) were added in serum-free medium and allowed to attach for 2 hours at 37° C. Cells were removed and the wells were washed twice with PBS and photographed.

Figure 2:
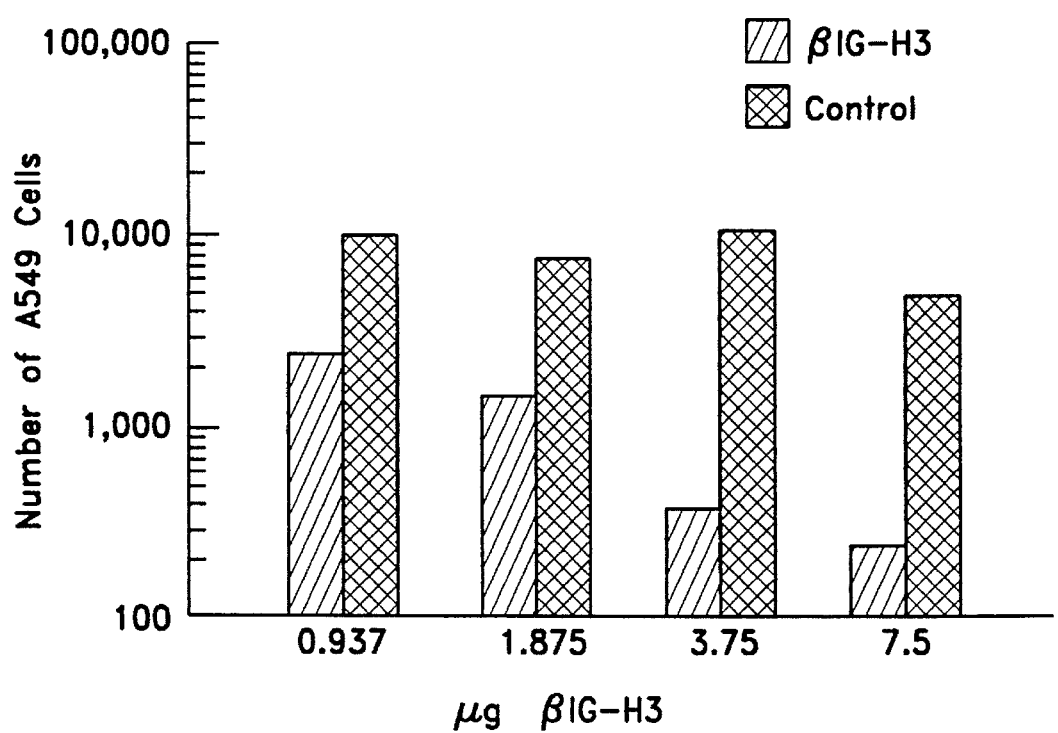
FIG. 2 shows the growth curve for H3-producing CHO cell clones. Control CHO/pEE-14, CHO/H3cl.A13 (A-13) and CHO/H3cl.A2 (A-2) cells were seeded at 5×10⁵ cells in 100 mm dishes, grown for the indicated times, trypsinized and counted. Data points represent the average of duplicate samples. The x-axis shows the cell growth time and the y-axis shows the cell number.

The results show that in the presence of H3, the cells did not attach to the wells. Conversely, attachment occurred after plating on equivalent amounts of BSA or control CHO/pEE-14 protein. This effect was concentration-dependent (FIG. 2). When A549 cells were plated in the presence of 7.5 μg H3, only about 200 cells remained attached to the plate; with 1.875 μg protein, about 2,500 cells remained attached. In contrast, when A549 cells were plated in the presence of 7.5 μg BSA, about 15,000 cells remained attached to the plate. Similar results were obtained with HeLa, WI-38 and CHO cells.

Surprisingly, carboxy-terminal sequencing of the recombinant H3 protein revealed that the RGD sequence was not present, most likely due to carboxy-terminal processing of H3. Therefore, it is possible that the anti-adhesion activity of H3 is not mediated through the RGD sequence. Hence, another sequence motif such as the PDSGR laminin adhesion domain or an as yet unidentified sequence motif may be responsible for the anti-adhesion activity mediated by H3.

EXAMPLE 5

Promotion of Fibroblast Adhesion by H3

Human foreskin fibroblasts isolated at Advanced Tissue Sciences, La Jolla, Calif., were grown in monolayer culture. This cell type is also available from American Type Culture Collection, Rockville, Md. (ATCC CRL 1634 and CRL 1635). Two hours before the experiment, cells were included in all subsequent washing and adhesion solutions. Cells were harvested by incubation with 0.25% trypsin in PBS lacking calcium and magnesium salts. Cells were washed twice with Dulbecco's Modified Eagle Medium (DMEM) containing 10% fetal bovine serum (FBS), twice with DMEM only, counted and resuspended in DMEM containing 10% heat treated bovine serum albumin (BSA).

Recombinant H3 was purified as described (Skonier et al, 1992). Recombinant H3 and human serum were diluted in water to a final volume of 100 ul and allowed to air-dry in the microtiter wells overnight. It is well known that the predominant cell adhesion protein present in serum is fibronectin. The proteins were rehydrated in 200 μl PBS for 15 minutes, removed and non-specific binding sites blocked with 1% BSA in PBS for 3 hours at room temperature. The PBS was removed and the wells were washed twice with 200 μl PBS. Approximately 30,000 human foreskin fibroblasts in 100 μl DMEM were added to each well and allowed to attach to the substrates at 37° C. At the appropriate times, cell attachment was quantitated by measuring absorbance at 405 nm of a p-nitrophenol derivatized chromogenic substrate for hexosaminidase as described by Landegren (*J. Immunol. Methods*, 67:379–388, 1984).

Figure 3:
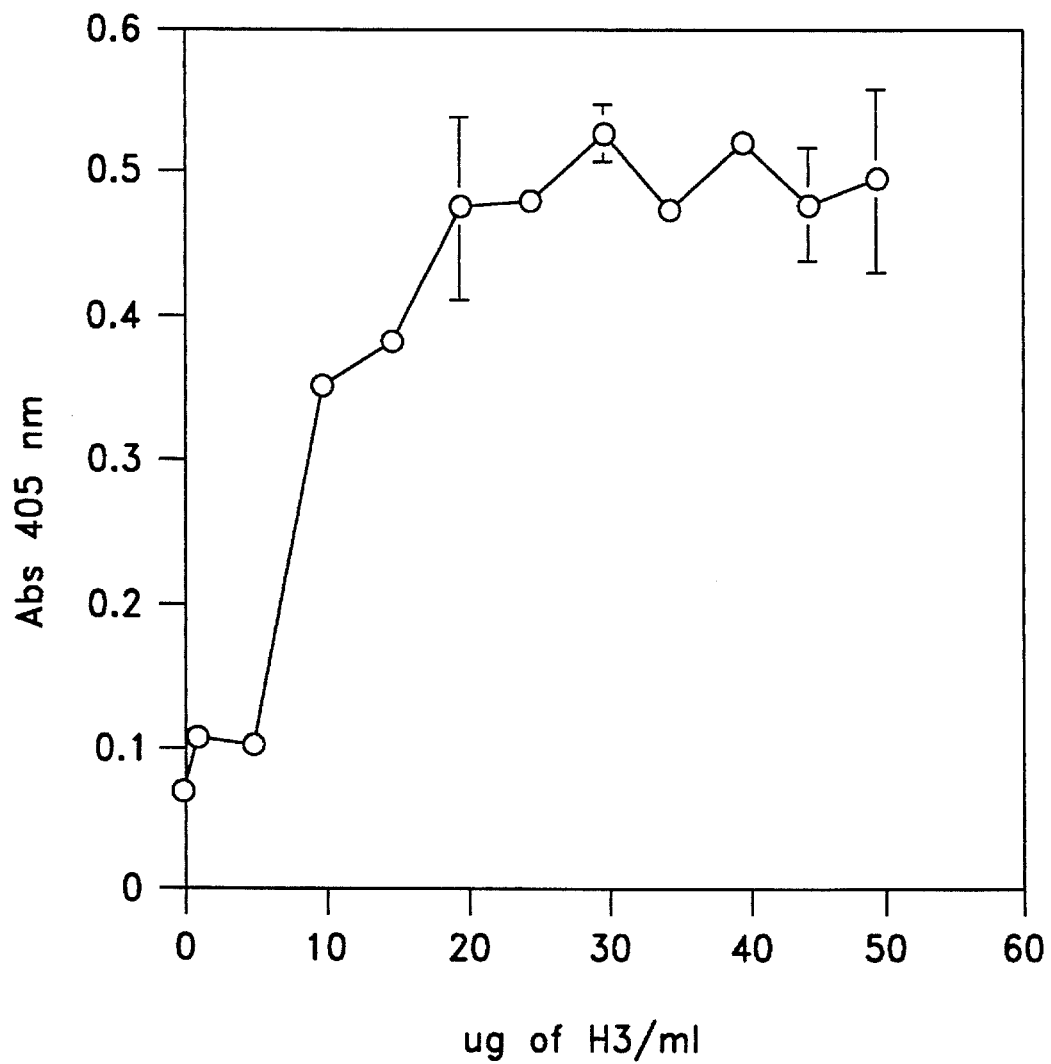
FIG. 3 is a graph showing the increase in human dermal fibroblast adherence with increasing concentrations of recombinant H3 after a 2.5 hour cell attachment period. The concentration of added H3 is shown on the x-axis and the cell adherence as reflected by the absorbance at 405 nm is shown on the y-axis.
Figure 4:
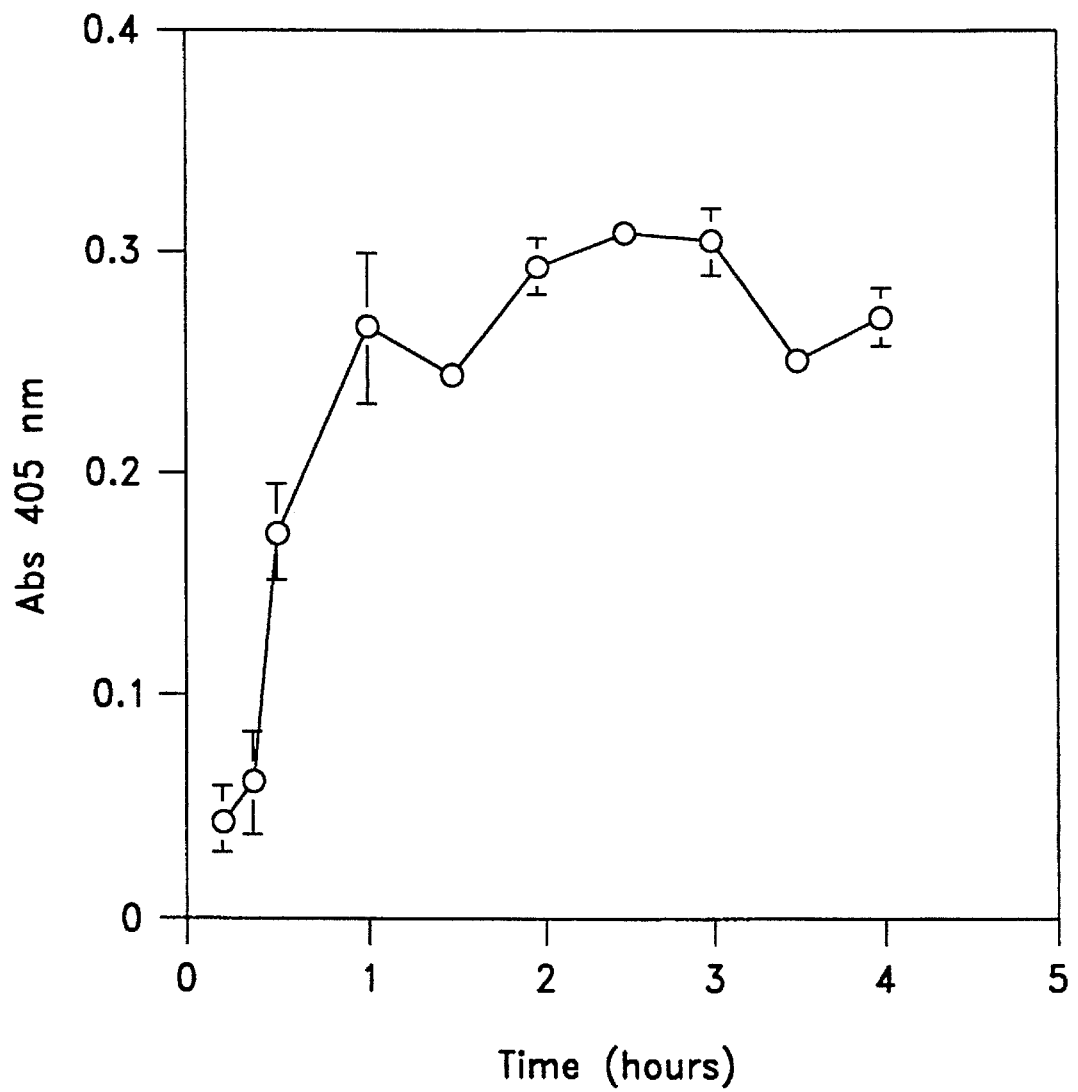
FIG. 4 is a graph illustrating the increase in fibroblast adherence to recombinant H3-coated microtiter wells over time. The adhesion time is shown on the x-axis and the absorbance at 405 nm is shown on the y-axis.

The results indicated that H3 promoted the attachment of human dermal fibroblasts in a concentration-dependent manner (FIG. 3). Maximum adhesion occurred at about 30 μg H3/well and remained fairly stable up to 50 μg H3/well. The optimum time for adhesion on the H3 substrate was approximately 2.5 hours (FIG. 4). Few cells plated on PBS-BSA adhered to the wells and those that did appeared rounded. In contrast, cells plated on serum-coated or H3-coated wells adhered very well and appeared elongated and spread out as determined by light microscopy. This indicates that H3 can promote the adhesion of dermal fibroblasts and has implications in tissue engineering to promote attachment and spreading of dermal fibroblasts on two and three dimensional scaffolds.

EXAMPLE 6

Production of H3 by Human Fibroblasts

Primary human foreskin fibroblasts (PHFF) were cultured in DMEM containing 10% FBS, 2 mM L-glutamine and minimal essential amino acids. Recombinant TGF-β was prepared as described (Gentry et al., *Mol. Cell Biol.*, 8:4162–4168) and used at 20 ng/ml).

Cells were metabolically labeled with 200 μCi/ml [$^{35}$]-translabel (ICN, Irvine, Calif.) in DMEM containing 5% dialyzed fetal calf serum for four hours, and either stimulated with TGF β or left untreated. Supernatants were immunoprecipitated with either anti-H3 antiserum or normal rabbit serum. Immunoprecipitates were analyzed by SDS-PAGE. Gels were dried and exposed to Fuji x-ray film (Sigma, St. Louis, Mo.). In both TGF β-treated and untreated cells, the anti-H3 antiserum immunoprecipitated a protein having a molecular weight of about 70 kDa. This protein was unreactive with normal rabbit serum. The amount of protein secreted into the culture medium by TGF β-stimulated cells was increased about three fold compared to unstimulated cells.

EXAMPLE 7

Acceleration of Wound Healing by H3

Patients having skin ulcers are topically administered 200 μg recombinant H3 prepared according to Example 1 daily in the form of a cream directly to one ulcer. A second ulcer is treated daily with a control cream lacking H3. The healing rate of both ulcers is monitored over time to show the acceleration of wound healing promoted by H3.

A similar experiment is also performed using an H3-coated three dimensional nylon mesh scaffold seeded with human dermal fibroblasts. The scaffold is applied to one ulcer, while a second ulcer is treated with an scaffold coated with only H3 and a third ulcer is treated with an empty scaffold. The improvement of the ulcers is monitored to show the promotion of wound healing by the fibroblast-coated nylon mesh scaffold.

It should be noted that the present invention is not limited to only those embodiments described in the Detailed Description. Any embodiment which retains the spirit of the present invention should be considered to be within its scope. However, the invention is only limited by the scope of the appended claims.

---

What is claimed is:

1. A method for accelerating skin wound healing comprising contacting said skin wound with an effective healing-promoting amount of H3 protein.

2. The method of claim 1, wherein said H3 protein is contained in a topical pharmaceutical formulation selected from the group consisting of: aqueous solution, gel, cream, paste, lotion, spray, suspension, dispersion, salve and ointment.

3. The method of claim 1, wherein said H3 protein is recombinant.

4. The method of claim 1, wherein said H3 protein is derived from human fibroblasts.

5. The method of claim 1, wherein said wound is selected from the group consisting of: skin ulcer, burn, laceration and surgical incision.

6. A method for accelerating skin wound healing comprising applying to said skin wound a solid support; H3 protein coated onto said solid support, and skin cells adhering to said H3 protein-coated solid support.

7. A method for accelerating skin wound healing comprising contacting said skin wound at least daily with between about 10 µg and about 10 mg H3 protein.

8. A method for accelerating skin wound healing comprising contacting said skin wound with a shaped article, said shaped article comprising a solid support coated with between about 0.1 µg/mm$^3$ and about 10 µg/mm$^3$ H3 protein and fibroblasts adhering to said H3 protein.

* * * * *